United States Patent [19]
Young et al.

[11] Patent Number: 4,666,928
[45] Date of Patent: May 19, 1987

[54] PROPYLPHENOXY PYRIDINE CARBOXYLATES AS LEUKOTRIENE ANTAGONISTS

[75] Inventors: Robert N. Young, Senneville; Joshua Rokach, Laval, both of Canada

[73] Assignee: Merck Frosst Canada, Ind., Kirkland, Canada

[21] Appl. No.: 645,596

[22] Filed: Aug. 30, 1984

[51] Int. Cl.$^4$ ............... C07D 213/55; A61K 31/44
[52] U.S. Cl. ............................ 514/350; 514/347; 514/348; 546/294; 546/295; 546/296; 546/298
[58] Field of Search ............... 546/294, 298, 295, 296; 514/350, 347, 348

[56] References Cited
U.S. PATENT DOCUMENTS
4,219,477  8/1980  Fujimoto et al. ............... 540/332

Primary Examiner—Alan L. Rotman
Attorney, Agent, or Firm—Gabriel Lopez; Hesna J. Pfeiffer; Paul H. Ginsburg

[57] ABSTRACT

Compounds having the formula:

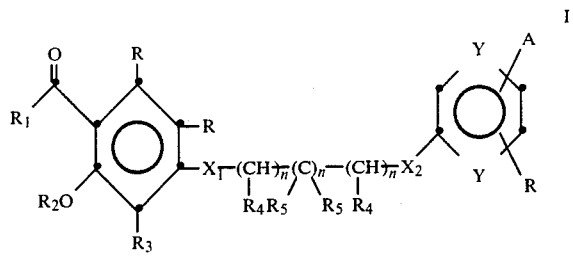

are antagonists of leukotrines of $C_4$, $D_4$ and $E_4$, the slow reacting substance of anaphylaxis. These compounds are useful as anti-asthmatic, anti-allergic and anti-inflammatory agents.

9 Claims, No Drawings

PROPYLPHENOXY PYRIDINE CARBOXYLATES AS LEUKOTRIENE ANTAGONISTS

This invention is directed to compounds which act as antagonists of the leukotrienes.

The leukotrienes are a novel group of biologically active mediators derived from arachidonic acid through the action of lipoxygenase enzyme systems. There are two groups of leukotrienes derived from the common unstable precursor Leukotriene $A_4$. The first of these are the peptido-lipid leukotrienes, the most important being Leukotrienes $C_4$ and $D_4$. These compounds collectively account for the biologically active material known as the slow reacting substance of anaphylaxis.

The leukotrienes are potent smooth muscle contracting agents, particularly on respiratory smooth muscle but also on other tissues (e.g. gall bladder). In addition, they promote mucous production, modulate vascular permeability changes and are potent inflammatory agents in human skin. The most important compound in the second group of leukotrienes is Leukotriene $B_4$, a dihydroxy fatty acid. This compound is a potent chemotactic agent for neutrophils and eosinophils and in addition, may modulate a number of other functions of these cells. It also effects other cell types such as lymphocytes and for example may modulate the action of T-suppressor cells and natural killer cells. When injected in vivo, in addition to promoting the accumulation of leukocytes, Leukotriene $B_4$ is also a potent hyperalgesic agent and can modulate vascular permeability changes through a neutrophil dependent mechanism. Both groups of leukotrienes are formed following oxygenation of arachidonic acid through the action of a 5-lipoxygenase enzyme. See for example, D. M. Bailey et al., *Ann. Rpts. Med. Chem.* 17 203 (1982).

The leukotrienes are potent spasmogens of human trachea, bronchus and lung parenchymal strips, and when administered to normal volunteers as aerosols are 3,800 times more potent that histamine at inducing a 50% decrease in air flow at 30% of vital capacity. They mediate increases in vascular permeability in animals and promote mucous production in human bronchial explants. In addition, Leukotriene $B_4$ may also mediate mucous production and could be an important mediator of neutrophil and eosinophil accumulation in asthamatic lungs. 5-Lipoxygenase products are also thought to be regulators of mast cell degranulation. In vitro studies have shown that antigen challenge of human lung results in the release of leukotrienes and in addition purified human mast cells can produce substantial amount of leukotrienes. There is therefore good evidence that leukotrienes are important mediators of human asthma. Leukotriene antagonists would therefore be a new class of drugs for the treatment of asthma.

Psoriasis is a human skin disease which effects between two and six percent of the population. There is no adequate therapy for psoriasis and related skin conditions. The evidence for leukotriene involvement in these diseases is as follows. One of the earliest events in the development of preparpillary lesions is the recruitment of leukocytes to the skin site. Injection of Leukotriene $B_4$ into human skin results in a pronounced neutrophil accumulation. There are gross abnormalities in arachidonic acid metabolism in human psoriatic skin. In particular, highly elevated levels of free arachidonic acid can be measured as well as large amounts of lipoxygenase products. Leukotriene $B_4$ has been detected in psoriatic lesions, but not in uninvolved skin, in biologically significant amounts.

Leukotrienes can be measured in nasal washings from patients with allergic rhinitis and are greatly elevated following antigen challenge. Leukotrienes may mediate this disease through their ability to regulate mast cell degranulation, by modulating mucous production and mucocillary clearance and by mediating the accumulation of inflammatory leukocytes.

Leukotrienes can also mediate other diseases. These include atopic dermatitis, gouty arthritis and gall bladder spasms. In addition, they may have a role in cardiovascular disease because leukotrienes $C_4$ and $D_4$ act as coronary and cerebral arterial vasoconstrictors and these compounds may also have negative inotropic effects on the myocardium. In addition, the leukotrienes are important mediators of inflammatory diseases through their ability to modulate leukocyte and lymphocyte function. See for example, B. Samuelsson, *Science,* 220 568 (1983).

Several classes of compounds exhibit ability to antagonize the action of leukotrienes in mammals, especially humans. See for example: Great Britain Patent Specification No. 2,058,785; and European Patent Application Nos. 56,172 and 61,800.

The compounds of the present invention may be used to treat or prevent mammalian (especially human) disease states such as erosive gastritis; erosive esophagitis; inflammatory bowel disease; ethanol-induced hemorrhagic erosions; hepatic ischemia; noxious agent induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure.

The present invention provides compounds that act as antagonists to prevent leukotriene action or as inhibitors to prevent synthesis. The present invention also provides compounds which prevent or reverse leukotriene action or prevent leukotriene synthesis when administered orally. The present invention also provides compounds which prevent or reverse leukotriene action or prevent leukotriene synthesis when administered by insufflation, intravenously, rectally, topically, parenterally including subcutaneously and intramuscularly, or nasally. The present invention also provides methods for the preparation of these compounds. The present invention also provides intermediates useful in the synthesis of these compounds. Finally, the present invention provides pharmaceutical formulations for administering these compounds.

The present invention relates to compounds having activity as leukotriene antagonists in mammals, especially humans, to methods for their preparation, to intermediates useful in their preparation and to methods for using these compounds. Because of their activity as leukotriene antagonists, the compounds of the present invention are useful as anti-asthmatic, anti-allergic, and anti-inflammatory agents and are useful in treating allergic rhinitis and chronic bronchitis and for amelioration of skin diseases like psoriasis and atopic exzema. These compounds are also useful to antagonize or inhibit the pathologic actions of leukotrienes on the cardiovascular and vascular systems.

The compounds of the present invention have the formula I:

$$\underset{R_3}{\underset{|}{\overset{\overset{O}{\underset{||}{R_1-C}}}{\underset{|}{R_2O}}}}\overset{R}{\underset{}{\bigcirc}}\overset{}{\underset{}{-R}}-X_1-(CH)_{\overline{n}}\underset{R_4R_5}{\overset{|}{(C)_n}}-(CH)_{\overline{n}}X_2\overset{Y}{\underset{Y}{\bigcirc}}\overset{A}{\underset{R}{}}$$ I wherein:

each Y is independently selected from CR or N, but at least one Y must be N;

each n is independently 0 to 6;

each R is independently H, OH, alkyl of 1 to 6 carbon atoms which may be straight chain or branched; alkenyl of 2 to 6 carbon atoms which may be straight chain or branched; trifluoromethyl; alkoxy of 1 to 6 carbon atoms which may be straight chain or branched; SH; thioalkyl of 1 to 6 carbon atoms which may be straight chain or branched; phenyl; phenyl substituted by alkyl of 1 to 3 carbon atoms or by halogen (i.e., fluorine, chlorine, bromine or iodine); benzyl; phenethyl; halogen; amino; $N(R_4)_2$; $COOR_4$; $CH_2OR_4$; formyl; CN; trifluoromethylthio; or nitro;

$R_1$ is H, alkyl of 1 to 6 carbon atoms which may be straight chain or branched; or alkoxy of 1 to 6 carbon atoms which may be straight chain or branched;

$R_2$ is H or alkyl of 1 to 6 carbons which may be straight chain or branched; $R_4CO$; or $R_4OCH_2$;

$R_3$ is alkyl of 1 to 6 carbon atoms which may be straight chain or branched; alkenyl of 3 to 6 carbon atoms which may be straight chain or branched; phenyl or phenyl substituted by one or more R;

each $R_4$ is independently H or alkyl of 1 to 6 carbon atoms which may be straight chain or branched;

each $R_5$ is independently H, OH, alkyl of 1 to 4 carbons, alkenyl or 3 to 6 carbon atoms, or both $R_5$'s may be combined to create a doubly bonded oxygen (=O) or doubly bonded $=C(R_4)_2$ group wherein $R_4$ is as defined above;

$X_1$ and $X_2$ are each independently oxygen, sulfur, sulfoxide, sulfone;

$$\underset{}{\overset{O}{\underset{||}{S}}}=NR_4;\ NR_4;\ \underset{}{\overset{O}{\underset{||}{N-C}}}-R_1;$$

N—CN; or $NCONHR_4$;

A is $$-\underset{R_6}{\overset{\overset{Z}{\underset{||}{(C)_p}}}{|}}-\underset{R_6}{\overset{\overset{R_4}{|}}{(C)_r}}-\left[\underset{}{\overset{\overset{R_8}{|}}{C}}=\underset{}{\overset{\overset{R_8}{|}}{C}}\right]_p-\underset{R_6}{\overset{\overset{R_4}{|}}{(C)_r}}-R_7$$

wherein the broken line represents an optional triple bond and

Z is O; S; H and OH; $CH_2$; alkenyl of 2 to 4 carbon atoms; N—$R_9$ wherein $R_9$ is OH, $N(R_4)_2$, alkyl or alkoxy of 1 to 6 carbon atoms which may be straight chain or branched, phenyl or phenyl substituted by one or more alkyl or alkoxy groups of 1 to 3 carbon atoms, halogen, hydroxy, haloalkyl, COOH, CN, formyl or acyl of 1 to 6 carbon atoms; and $R_4$ is as defined above;

each $R_6$ is independently H, OH or alkyl of 1 to 4 carbon atoms;

each p is independently 0 to 2; and each r is independently 0 to 4;

$R_7$ is $COOR_4$; $CH_2OH$; CHO; tetrazole; CONH-$SO_2R_9$; $NHSO_2R_9$; hydroxymethylketone; acetoxymethylketone; CN; $CON(R_4)_2$; a monocyclic or bicyclic heterocyclic ring containing an acidic hydroxyl group; or $$-COO(CH_2)_s-\underset{R_4}{\overset{\overset{R_4}{|}}{C(CH_2)_s}}-R_{10}$$

wherein each s is independently 0 to 3; $R_{10}$ is (A) a monocyclic or bicyclic heterocyclic radical containing from 3 to 12 nuclear carbon atoms and 1 or 2 nuclear heteroatoms selected from N and S with at least one being N, and with each ring in the heterocyclic radical being formed of 5 or 6 atoms, or (B) the radical W—$R_{11}$ wherein W is O, S or NH and $R_{11}$ contains up to 21 carbon atoms and is (1) a hydrocarbon radical or (2) an acyl radical of an organic acyclic or monocyclic carboxylic acid containing not more than 1 heteroatom in the ring; and $R_4$ is as defined above;

each $R_8$ is independently H, or alkyl of 1-4 carbons, and is absent when a triple bond is present;

and a pharmaceutically acceptable salt or acid addition salt thereof.

A preferred group of formula I compounds are those in which $X_1$ is O, $X_2$ is O, S, SO, $SO_2$, NH, or N—CN, one Y is N and the other is CH, each n is 1, A is $$-\underset{R_6}{\overset{\overset{R_4}{|}}{(C)_r}}-\underset{R_6}{\overset{\overset{R_4}{|}}{(C)_r}}-R_7$$

wherein $R_4$, $R_6$ and $R_7$ are as defined for formula I, and the remaining substituents are as defined above.

A more preferred embodiment are compounds of Formula Ia:

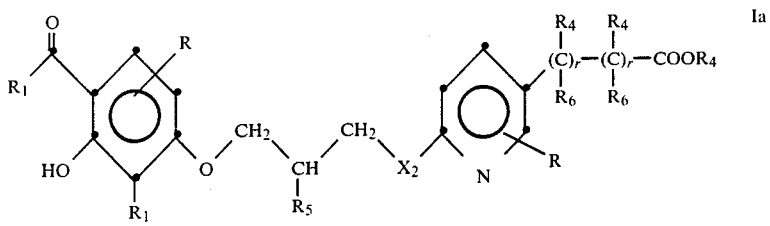

wherein

R is as defined for Formula I; each $R_1$ is alkyl of 1 to 6 carbon atoms which may be straight chain or branched;

$R_4$ is as defined for Formula I;
$R_5$ is as defined for Formula I;
$R_6$ is as defined for Formula I;
$X_2$ is S or $SO_2$; and
each r is independently 0 to 2.

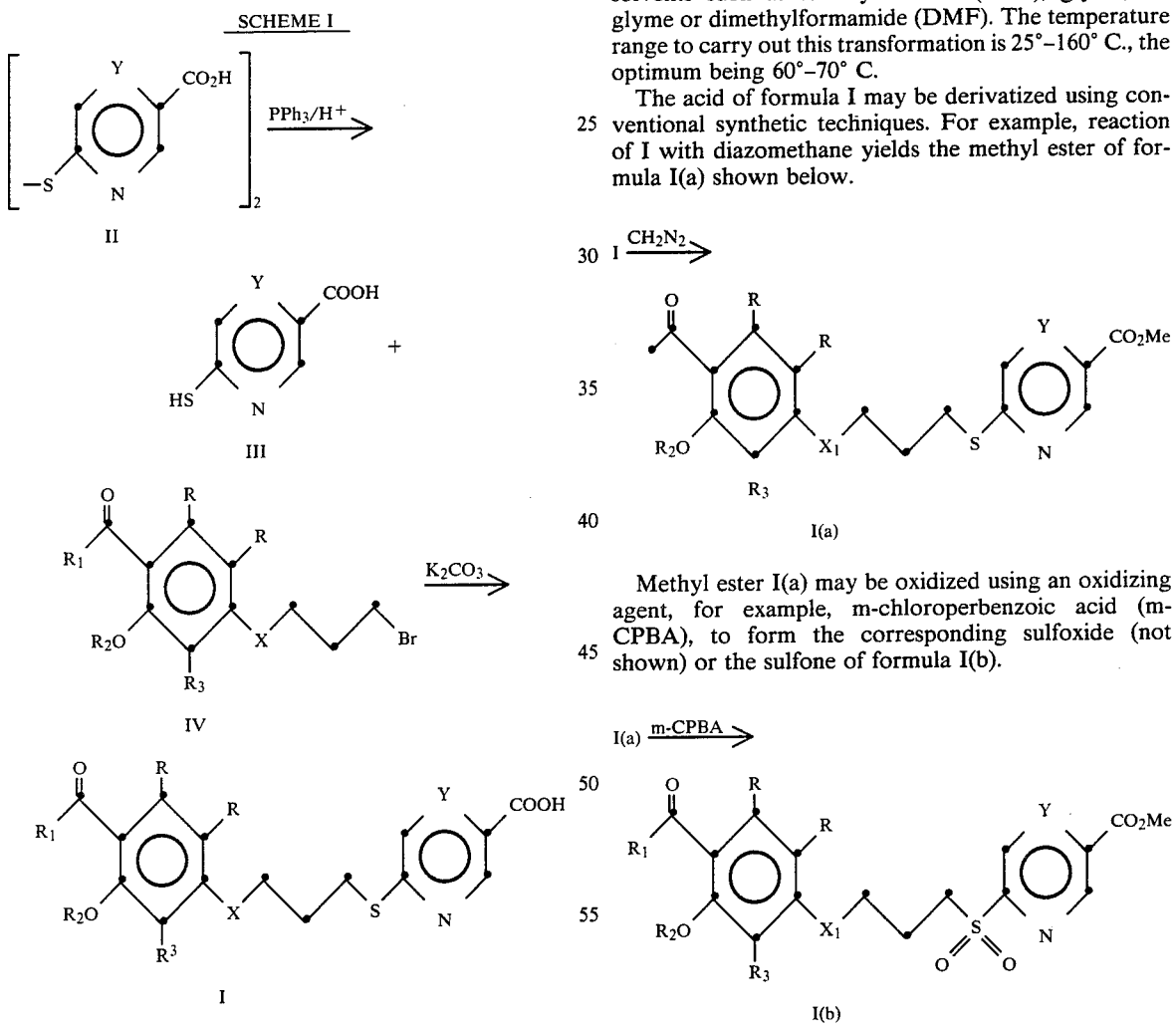

The compounds of the present invention may be prepared by several different routes. According to one method, illustrated in Scheme I, a compound of formula II is reacted with triphenylphosphine, and acid to yield the unisolated intermediate III. Reaction of III with bromide of formula IV or its corresponding chloride, or iodide in the presence of a base, such as potassium carbonate in a solvent such as methyl ethyl ketone yields the compound of formula I. Other suitable bases could be an alkali metal carbonate such as $Li_2CO_3$, or $Na_2CO_3$. The reaction could also be carried out in other solvents such as tetrahydrofuran (THF), glyme, diglyme or dimethylformamide (DMF). The temperature range to carry out this transformation is 25°–160° C., the optimum being 60°–70° C.

The acid of formula I may be derivatized using conventional synthetic techniques. For example, reaction of I with diazomethane yields the methyl ester of formula I(a) shown below.

Methyl ester I(a) may be oxidized using an oxidizing agent, for example, m-chloroperbenzoic acid (m-CPBA), to form the corresponding sulfoxide (not shown) or the sulfone of formula I(b).

Hydrolysis of the methyl ester sulfone of formula I(b), using conventional techniques such as treatment with aqueous base, followed by treatment with aqueous acid, yields the free acid sulfone of formula I(c).

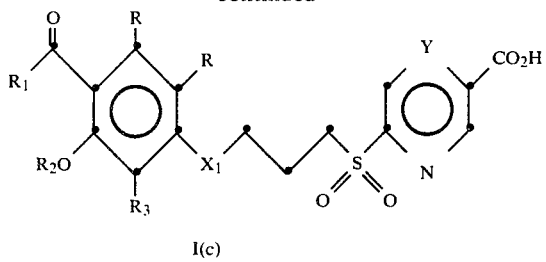

I(c)

The free acid compound of formula I may also be derivatized by reaction with oxalyl chloride to yield the acid chloride of formula V. Reaction of the acid chloride V with diazomethane yields the diazomethyl species of formula VI.

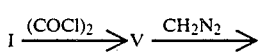

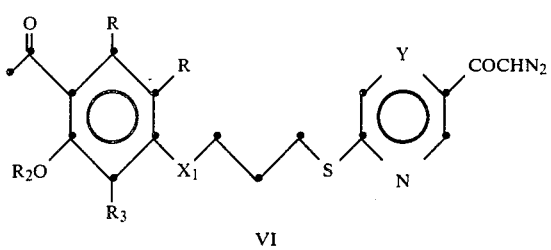

VI

Reaction of the compound of formula VI with acetic acid yields the compound of formula I(d).

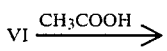

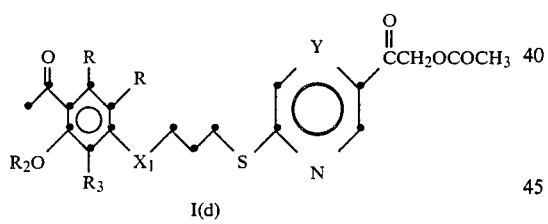

I(d)

Reaction of the compound of formula VI with silver oxide yields the compound of formula I(e).

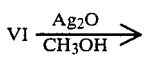

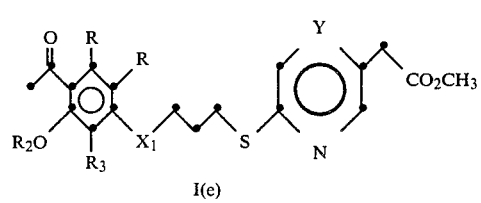

I(e)

Following the reaction scheme shown above for the compound for formula I(a), compound I(e) may be similarly treated to produce the free acid of formula I(f) and the sulfone methyl ester of formula I(g). The sulfone methyl ester of formula I(g) may be readily hydrolyzed to yield the sulfone free acid of formula I(h).

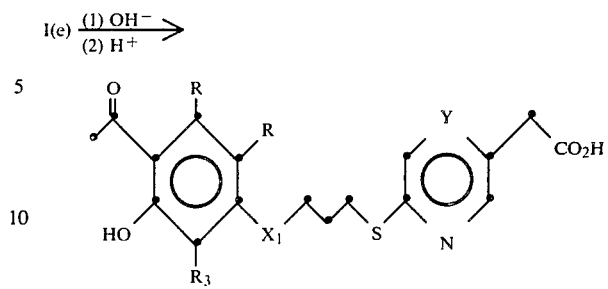

I(f)

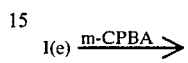

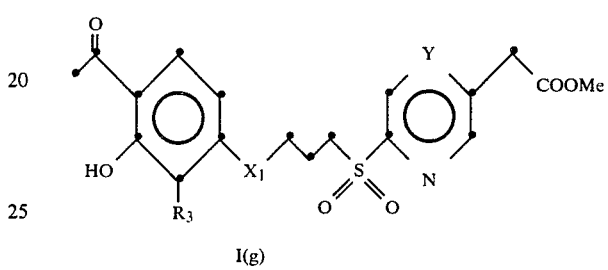

I(g)

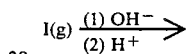

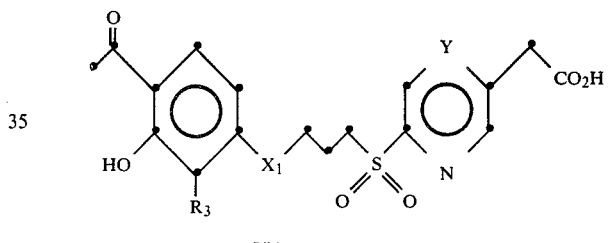

I(h)

In those instances when assymetric atoms are present, more than one stereoisomer is possible, and all possible isomeric forms are deemed to be included within the planar structural representations shown. Optically active (R) and (S) isomers may be resolved using conventional techniques known to the skilled artisan.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced lesion assay and (B) an indomethacin-induced ulcer assay.

A. Ethanol-Induced Gastric Ulcer Assay

Twenty-four hour fasted Sprague-Dawley (S.D.) rats are perorally (p.o.) dosed with 1.0 ml absolute ethanol. Fifteen to thirty minutes prior to ethanol administration, groups of rats each receive either an aqueous vehicle (aqueous methylcellulose 5% wt.) or the test compound at various doses perorally. One hour later, the animals are sacrificed and stomach mucosae are examined for resulting lesions.

B. Indomethacin-Induced Ulcer Assay

Indomethacin, 10mg/kg p.o., is used to induce ulcers in 24 hour fasted S.D. rats. Fifteen minutes prior to indomethacin administration, groups of rats each receive either an aqueous vehicle (5% by weight methylcellulose) or the test compound at various doses perorally. Four hours later the animals are sacrificed and stomach mucosae are examined for resulting ulcers.

The magnitude of a prophylactic or therapeutic dose of a compound of formula I will, of course, vary within the nature of the severity of the condition to be treated and with the particular compound of formula I and its route of administration. In general, the daily dose range for anti-asthmatic, anti-allergic or anti-inflammatory use lies within the range of from about 0.01 mg to about 100 mg per kg body weight of a mammal.

The exact amount of a compound of formula I to be used as a cytoprotective agent will depend on, inter alia, whether it is being administered to heal damaged cells or to avoid future damage, on the nature of the damaged cells (e.g., gastro-intestinal ulcerations vs. nephrotic necrosis), and on the nature of the causative agent. An example of the use of a compound of the formula I in avoiding future damage, would be co-administration of a compound of the formula I with a non-steroidal anti-inflammatory drug (for example, indomethacin) that might otherwise cause such damage.

The effective daily dosage level for compounds of Formulae I inducing cytoprotection in mammals, especially humans, will generally range from about 0.002 mg/kg to about 100 mg/kg, preferably from about 0.02 mg/kg to about 30 mg/kg. The dosage may be administered in single or divided individual doses.

Any suitable route of administration may be employed for providing a mammal, especially a human with an effective dosage of a leukotriene antagonist. For example, oral, rectal, transdermal, parenteral, intramuscular, intravenous and the like may be employed. Dosage forms include tablets, troches, dispersions, suspensions, solutions, capsules and the like.

The pharmaceutical compositions of the present invention comprise a compound of formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived frm inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. The compositions include compositions suitable for oral, rectal, ophthalmic, pulmonary, nasal, dermal, topical or parenteral (including subcutaneous, intramuscular and intravenous) administration, although the most suitable route in any given case will depend on the nature and severity of the conditions being treated and on the nature of the active ingredient. They may be conveniently presented in unit dosage form and prepared by any of the methods well-known in the art of pharmacy.

For use where a composition for intravenous administration is employed, a suitable dosage range for anti-asthmatic, anti-inflammatory or anti-allergic use is from about 0.01 mg to about 20 mg (preferably from about 0.1 mg to about 10 mg) of a compound of formula I per kg of body weight per day and for cytoprotective use from about 0.002 mg to about 100 mg (preferably from about 0.02 mg to about 30 mg and more preferably from about 0.1 mg to about 10 mg) of a compound of Formula I per kg of body weight per day. In the case where an oral composition is employed, a suitable dosage range for anti-asthmatic, anti-inflammatory or anti-allergic use is, e.g. from about 1 to about 100 mg of a compound of formula I per kg of body weight per day, preferably from about 5 mg to about 40 mg per kg and for cytoprotective use from about 0.01 mg to about 100 mg (preferably from about 0.1 mg to about 30 mg and more preferably from about 0.1 mg to about 10 mg) of a compound of Formula I per kg of body weight per day.

For administration by inhalation, the compounds of the present invention are conveniently delivered in the form of an aerosol spray presentation from pressurized packs or a nebuliser. The preferred composition for inhalation is a powder which may be formulated as a cartridge from which the powder composition may be inhaled with the aid of a suitable device. In the case of a pressurized aerosol, the dosage unit may be determined by providing a value to deliver a metered amount.

In practical use, leukotriene antagonists of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or intravenous. In preparing the compositions for oral dosage form, any of the usual pharmaceutical media may be employed, such as, for example, water glycols, oils, alcohols, flavoring agents, preservatives, coloring agents and the like in the case of oral liquid preparations, such as, for example, suspensions, elixirs and solutions; or carriers such as starches, sugars, diluents, granulating agents, lubricants, binders, disintegrating agents and the like in the case of oral solid preparations such as, for example, powders, capsules and tablets. Because of their ease of administration, tablets and capsules represent the most advantageous oral dosage unit form, in which case solid pharmaceutical carriers are obviously employed. If desired, tablets may be sugar coated or enteric coated by standard techniques.

In addition to the common dosage forms set out above, the leukotriene antagonists of Formula I may also be administered by controlled release means and/or delivery devices such as those described in U.S. Pat. Nos. 3,845,770; 3,916,899; 3,536,809; 3,598,123;

3,630,200 and 4,008,719, the disclosure of which is hereby incorporated herein by reference.

Pharmaceutical compositions of the present invention suitable for oral administration and by inhalation in the case of asthma therapy may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, lubricating, surface active or dispersing agent. Molded tablets may be made by molding in a suitable machine, a mixture of the powdered compound moistened with an inert liquid diluent. Desirably, each tablet contains from about 25 mg to about 500 mg of the active ingredient and each cachet or capsule contains from about 25 to about 500 mg of the active ingredient.

The following are examples of representative pharmaceutical dosage forms for the leukotriene antagonists of Formulae I:

| Injectable Suspension | mg/ml |
|---|---|
| Compound of Formula I | 2 |
| Methylcellulose | 5.0 |
| Tween 80 | 0.5 |
| Benzyl alcohol | 9.0 |
| Methyl paraben | 1.8 |
| Propyl paraben | 0.2 |
| Water for injection to a total volume of 1 ml | |

| Tablet | mg/tablet |
|---|---|
| Compound of Formula I | 25.0 |
| Microcrystalline Cellulose | 325.0 |
| Providone | 14.0 |
| Microcrystalline Cellulose | 90.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

In addition to the compounds of Formula I, the pharmaceutical compositions can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID, the weight ratio of the compound of the Formula I to the NSAID will generally range from about 200:1 to about 1:200. Combinations of a compound of the Formula I and other active ingredients will generally also be within the aforementioned range, but in each case, an effective dose of each active ingredient should be used.

Combinations of a compound of the Formula I and other active ingredients will generally be in the aforementioned ratios.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams
or a pharmaceutically acceptable salt thereof.

The propionic acid derivatives which may be used comprise: ibuprofen, ibuprufen aluminum, indoprofen, ketoprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Structurally related propionic acid derivatives having similar analgesic and anti-inflammatory properties are also intended to be included in this group.

Thus, "propionic acid derivatives" as defined herein are non-narcotic analgesics/non-steriodal anti-inflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$Na$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structurally related acetic acid derivatives having similar analgesic and antiinflammatory properties are also intended to be encompassed in this group.

Thus, "acetic acid derivatives" as defined herein are non-narcotic analgesics/non-steroidal anti-inflammatory drugs having a free —CH$_2$COOH group (which optionally can be in the form of a pharmaceutically acceptable salt group, e.g. —CH$_2$COO$^-$Na$^+$), typically attached directly to a ring system, preferably to an aromatic or heteroaromatic ring system.

The fenamic acid derivatives which may be used comprise: mefenamic acid, meclofenamic acid, flufenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

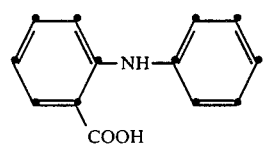

which can bear a variety of substituents and in which the free —COOH group can be in the form of a pharmaceutically acceptable salt group, e.g., —COO⁻Na⁺.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steriodal anti-inflammatory drugs which contain the basic structure:

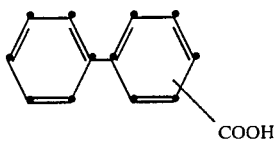

which can bear a variety of substituents and in which the free —COOH group can be in the form of a pharmaceutically acceptable salt group, e.g., —COO⁻Na⁺.

The oxicams which can be used in the present invention comprise: piroxicam, sudoxicam, isoxicam and 4-hydroxyl-1,2-benzothiazine 1,1-dioxide 4-(N-phenyl)-carboxamide. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

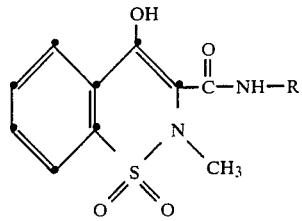

wherein R is an aryl or heteroaryl ring system.

The following NSAIDs may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, fluoxaprofen, fluproquazone, fopirtoline, fosfosal, flurcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin clonixinate, meclofenamate sodium, meseclazone, microprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

The following NSAIDs, designated by company code number, may also be used: 480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TVX2706, U60257, and WY41770.

Finally, NSAIDs which may also be used include the salicylates, specifically aspirin, and the phenylbutazones, and pharmaceutically acceptable salts thereof.

Pharmaceutical compositions comprising the Formula I compounds may also contain inhibitors of the biosynthesis of the leukotrienes such as are disclosed in pending U.S. patent applications Ser. No. 539,342, filed Oct. 5, 1983, Ser. No. 459,924, filed Jan. 21, 1983, Ser. No. 539,215, filed Oct. 5, 1983, and Ser. No. 547,161, filed Oct. 31, 1983, which are hereby incorporated herein by reference.

The compounds of the Formula I may also be used in combination with leukotriene antagonists such as those disclosed in copending applications U.S. Ser. Nos. 520,051 and 520,052, filed Aug. 5, 1983 which are hereby incorporated herein by reference and others known in the art such as those disclosed in European Patent Application Nos. 56,172 and 61,800; and in U.K. Patent Specification No. 2,058,785, which are hereby incorporated herein by reference.

Pharmaceutical compositions comprising the Formula I compounds may also contain as the second active ingredient, antihistaminic agents such as benadryl, dramamine, histadyl, phenergan and the like. Alternatively, they may include prostaglandin antagonists such as those disclosed in European Patent Application No. 11,067 or thromboxane antagonists such as those disclosed in U.S. Pat. No. 4,237,160. They may also contain histidine decarboxyase inhibitors such as α-fluoromethylhistidine, described in U.S. Pat. No. 4,325,961. The compounds of the Formula I may also be advantageously combined with an $H_1$ or $H_2$-receptor antagonist, such as for instance cimetidine, ranitidine, terfenadine, famotidine, aminothiadiazoles and like compounds, such as those disclosed in U.S. Pat. Nos. 4,283,408; 4,362,736; 4,394,508; or European Patent Application No. 40,696. The pharmaceutical compositions may also contain a $K^+/H^+$ ATPase inhibitor such as omeprazole, disclosed in U.S. Pat. No. 4,255,431, and the like. Each of the references referred to in this paragraph is hereby incorporated herein by reference.

The following examples illustrate the present invention without, however, limiting the same thereto. All temperatures are expressed in degrees Celsius.

EXAMPLE 1

2-(3-(4-Acetyl-3-hydroxy-2-propylphenoxy)propylthio)-5-carboxypyridine 5,5'-bis Carboxypyridyldisulfide (4.0 g, 12.97 mmoles) was taken up in DMF (about 350 ml) and H₂O (80 ml) with 4 drops of concentrated HCl. The reaction was warmed to dissolve the solids. Triphenylphosphine (3.74 g, 1.1 eq.) was then added and the reaction mixture was stirred at room temperature under N₂ for two hours. K₂CO₃ (5 eq., 9 g) was added followed by 4-(3-bromopropoxy)-3-propyl-2-hydroxyacetophenone (1 eq., 4.1 g). The reaction mixture was then heated at reflux (90°) for 10 hours. The DME was removed in vacuo. The aqueous phase was filtered, acidified and extracted into CHCl$_3$. The combined organic extracts were dried and concentrated in vacuo. The residue was purified via silica gel chromatography to provide the title compound, recrystallized from CHCl$_3$, m.p. 145°–147°.

Analysis, calculated: C, 61.68; H, 5.95; S, 8.23. Found: C, 61.61; H, 6.03; S, 8.58.

EXAMPLE 2

Methyl 2-(3-(4-acetyl-3-hydroxy-2-propylphenoxy)-propylthio)pyridine-5-carboxylate The compound of Example 1 (500 mg, 1.284 mmoles) was dissolved in a mixture of CH$_3$OH (10 ml) and ether (10 ml) cooled to 0° C. Diazomethane was added until a slight yellow color persisted. The reaction mixture was concentrated to afford the title compound, m.p. 66°–68°.

EXAMPLE 3

Methyl 2-(3-(4-acetyl-3-hydroxy-2-propylphenoxy)-propylsulfonyl)pyridine-5-carboxylate To a solution of the compound of Example 2, (517 mg, 1.284 mmoles) in CH$_2$Cl$_2$ (50 ml) at room temperature under N$_2$ was added m-CPBA (85%, 520 mg). The reaction mixture was stirred at room temperature for two hours. Additional m-CPBA (50 mg) was added and stirring was continued. Ca(OH)$_2$ (500 mg) was added and the mixture was stirred for ten minutes, filtered through Celite and concentrated. The residue was purified by chromatography on silica gel to afford the title compound, m.p. 114°–116°.

EXAMPLE 4

2-(3-(4-Acetyl-3-hydroxy-2-propylphenoxy)propylsulfonly)-5-carboxypyridine

The compound of Example 3, (570 mg, 1.31 mmoles) was dissolved in THF (6 ml) to which was added 1N NaOH (3 ml) and H$_2$O (3 ml). The reaction mixture was stirred at room temperature under N$_2$ overnight. The THF was removed in vacuo. The aqueous phase was washed with CHCl$_3$. Then the aqueous phase was acidified with concentrated HCl until slightly acid (pH about 5–6). The resulting beige solid was filtered, taken up in CHCl$_3$ (about 500 ml), and the organic solvent was dried and concentrated. The residue was triturated with ether and filtered to afford the title compound, m.p. 117°–179°.

Analysis, calculated: C,57.00; H, 5.50; S, 7.61. Found: C, 57.10; H, 5.67; S, 7.68.

EXAMPLE 5

2-(3-(4-Acetyl-3-hydroxy-2-propylphenoxy)propylthio)-5-(2-diaza-1-oxoethyl)pyridine The compound of Example 1, (2.0 g, 5.135 mmoles) was suspended in dry toluene (100 ml) containing 3 drops of DMF. Oxalyl chloride was added dropwise until evolution of gas ceased. The reaction mixture was then concentrated in vacuo. The residue was taken up in toluene (50 ml) and added dropwise to a solution of freshly prepared diazomethane at −30° C., then stored in the freezer overnight. The excess diazomethane was removed from the reaction mixture by bubbling air through the system for 1½ hours. The solvent was removed in vacuo to yield the title compound as yellow solid, m.p. 71°–73°, which was used as such in the next example.

EXAMPLE 6

2-(3-(4-Acetyl-3-hydroxy-2-propylphenoxy)propylthio)-5-(2-methoxy-2-oxoethyl)pyridine The entire product of Example 5 was dissolved in methanol (about 200 ml) and brought to reflux. Silver oxide (500 mg) was added (evolution of gas) and the reaction was refluxed 30 minutes. Additional silver oxide (1 g) was added and refluxing was continued for one additional hour. The reaction mixture was then cooled to room temperature, filtered and concentrated. The residue was purified on HPLC using 10/2 toluene/ethyl acetate as eluent to afford the title compound. NMR (CDCL$_3$): 1.0 (3H, m), 1.6 (2H, m), 2.25 (2H, m), 2.58 (3H, s), 2.60 (2H, m), 3.40 (2H, m), 3.60 (2H, s), 3.75 (3H, s), 4.20 (2H, m), 6.48 (1H, d), 7.25–7.8 (3H, m) 8.4 (1H, m), 12.8 (1H, s).

EXAMPLE 7

2-(3-(4-Acetyl-3-hydroxy-2-propylphenoxy)propylthio9-5-carboxymethylpyridine

The compound of Example 6, (700 mg, 1.677 mmoles) was taken up in THF (8 ml) to which was added 2 eq. 1N NaOH (3.7 ml) and H$_2$O (4.3 ml). The reaction mixture was stirred at room temperature under N$_2$. After two hours, the THF was removed in vacuo and the aqueous phase was diluted with H$_2$O (25 ml), then extracted with CHCl$_3$. The aqueous phase was acidified with concentrated hydrochloric acid, extracted into CHCl$_3$, and the organic extracts were dried and concentrated. The title compound was crystallized from CH$_3$OH, m.p. 124°–126°.

Analysis, calculated: C, 62.51; H, 6.24; S, 7.95. Found: C, 62.50; H, 6.18; S, 7.70.

EXAMPLE 8

2-(3-(4-Acetyl-3-hydroxy-2-propylphenoxy)propylsulfonyl)-5-(2-methoxy-2-oxoethyl)pyridine The compound of Example 6, (900 mg, 2.155 mmoles) was taken up in CH$_2$Cl$_2$ (30 ml) under N$_2$ at room temperature. To this solution was added m-CPBA (85%, 440 mg) and the reaction mixture was stirred at room temperature. After 1 hours, additional m-CPBA (440 mg) was added and stirring was continued. After 3 hours, the reaction mixture was stirred 10 minutes with Ca(OH)$_2$ (1 g) then filtered through Celite, concentrated in vacuo in the title compound crystallized from ethyl acetate, m.p. 124°–126°.

EXAMPLE 9

2-(3-(4-Acetyl-3-hydroxy-2-propylphenoxy)propylsulfonyl)-5-carboxymethylpyridine The compound of Example 8, (700 mg, 1.56 mmoles) was taken up in a mixture of THF (14 ml), 2 eq. 1N NaOH (3.3 ml) and H$_2$O (10 ml). The reaction mixture was stirred at room temperature under N$_2$ for 2 hours. The THF was removed in vacuo. The aqueous phase was extracted with ether, then acidified with HCl and extracted into CHCl$_3$. The combined organic extracts were dried and concentrated. The residue was triturated with ether to afford the title compound, m.p. 154°-156°.

Analysis, calculated: C, 57.92; H, 5.79; S, 7.36. Found: C, 57.93; H, 5.83; S, 7.59.

EXAMPLE 10

2-(3-(4-Acetyl-3-hydroxy-2-propylphenoxy)propylthio-5-(2-acetoxy-1-oxoethyl)pyridine The compound of Example 5, (600 mg, 1.451 mmoles) was added as a solid to 100 ml of refluxing glacial acetic acid and heated to about 100°. A slow evolution of gas was observed. Heating was continued for approximately 3 hours. The reaction mixture was concentrated in vacuo. The residue was purified on HPLC to afford the title compound, m.p. 93°-95°.

Analysis, calculated: C, 62.01; H, 6.11; S, 7.20. Found: C, 62.15; H, 6.10; S, 7.20.

The compounds of U.S. Ser. No. 520,052 have the formulae:

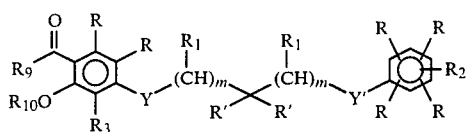

XI and

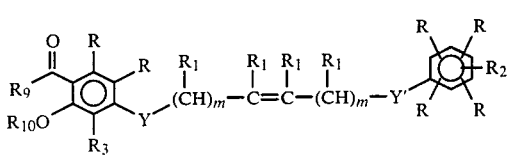

XII wherein
each R is independently H, OH, alkyl of 1 to 6 carbon atoms which may be straight chain or branched; alkenyl of 2 to 6 carbon atoms which may be straight chain or branched; trifluoromethyl; alkoxy of 1 to 6 carbon atoms which may be straight chain or branched; SH; thioalkyl of 1 to 6 carbon atoms which may be straight chain or branched; phenyl; phenyl substituted by alkyl of 1 to 3 carbon atoms or by halogen; benzyl; phenalkyl with from 2 to 4 alkyl carbon atoms; halogen, amino; $N(R_4)_2$ wherein $R_4$ is H or alkyl of 1 to 6 carbon atoms which may be straight chain or branched; $COOR_4$; $CH_2OR_4$; formyl; CN; trifluoromethylthio; or nitro;

each R' is independently $R_4$; $OR_4$; $COOR_4$; $N(R_4)_2$; $SR_4$; $CH_2OR_4$; CHO; or together R' and R' are O; $CH_2$; or

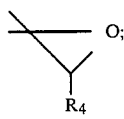

Y is oxygen, sulfur, sulfoxide, sulfone;

wherein $R_{11}$ is alkyl of 1-4 carbon atoms which may be straight chain or branched; $NR_{12}$ wherein $R_{11}$ is H, alkyl of 1-4 carbon atoms which may be straight chain or branched; or

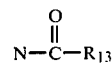

wherein $R_{13}$ is alkyl of 1-4 carbon atoms which may be straight chain or branched, alkoxy of 1-4 carbon atoms which may be straight chain or branched; or N—CN;

Y' is Y, —$CH_2$— or

each $R_1$ is independently hydrogen or alkyl of 1-3 carbon atoms;
each m is independently an integer from 0-6; and $R_2$ is

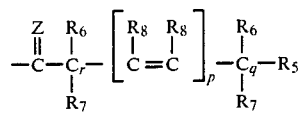

wherein Z is O, S, $CH_2$, H and OH, alkenyl of 1-4 carbons; or N—$R_{14}$ wherein $R_{14}$ is OH, alkyl or alkoxy of 1 to 6 carbon atoms, perhaloalkyl of 1 to 6 carbon atoms, phenyl or phenyl substituted by alkyl or alkoxy groups of 1 to 3 carbon atoms, halogen, hydroxy, haloalkyl, COOH, CN, formyl or acyl of 1 to 6 carbon atoms;

each $R_6$ is independently H or alkyl of 1-4 carbons;
each $R_7$ is independently H, OH, or alkyl of 1-4 carbons;
each $R_8$ is independently H, or alkyl of 1-4 carbons, and is absent when a triple bond is present;

$R_5$ is $COOR_4$; $CH_2OH$; CHO; tetrazole; $NHSO_2R_{14}$; $CONHSO_2R_{14}$; hydroxymethylketone; CN; $CON(R_7)_2$; a monocyclic or bicyclic heterocyclic ring containing an acidic hydroxyl group; or $COOR_{15}$ where $R_{15}$ is:

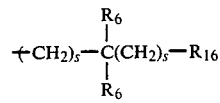

wherein each s is independently 0-3; $R_{16}$ is
(A) a monocyclic or bicyclic heterocyclic radical containing from 3 to 12 nuclear carbon atoms and 1 or 2 nuclear heteroatoms selected from N and S with at least one being N, and with each ring in the heterocyclic radical being formed of 5 or 6 atoms, or
(B) the radical W—$R_{17}$ wherein W is O, S or NH and $R_{17}$ contains up to 21 carbon atoms and is (1) a hydrocarbon radical or (2) an acyl radical of an organic acyclic or monocyclic carboxylic acid containing not more than 1 heteroatom in the ring;

r an q are each independently 0-20 provided that the total of r and q does not exceed 20; and
p is 0 or 1;
$R_3$ is alkyl of 1 to 6 carbon atoms which may be straight chain or branched; or alkenyl of 3 to 6 carbon atoms which may be straight chain or branched as illustrated in Formulae IV and V;

$R_9$ is alkyl of 1 to 6 carbon atoms which may be straight chain or branched; alkoxy of 1 to 6 carbon atoms which may be straight chain or branched; or $(CH_2)_rR_5$;

$R_{10}$ is H; alkyl of 1 to 6 carbon atoms which may be straight chain or branched;

or $R_4OCH_2$—;

and a pharmaceutically acceptable salt or acid addition salt thereof.

As used herein, the terms "each independently" or the equivalents thereof are employed to describe a number of possible position isomers and/or structural variations. For example, as described above, $R_2$ is:

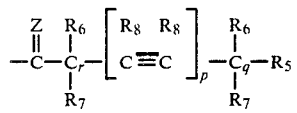

The letters r and q, represent possible alkane chains of from 0–20 carbon atoms, each having the $R_6$ and $R_7$ substituent groups. On each carbon atom of the alkane chain, the $R_6$ and/or $R_7$ substituent may be different. The above description therefore contemplates structures such as the following for the segments —$(CR_6R_7)_r$— and —$(CR_6R_7)_9$—;

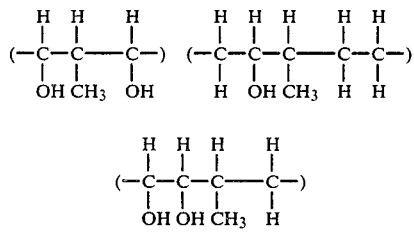

and the like.

The compounds of the present invention may be prepared by several different routes. According to one method a compound of Formula I is reacted with an optionally alkyl substituted alkenyl halide of Formula II wherein X is halogen and each $R_6$ is independently H or alkyl of 1–4 carbon atoms to yield the corresponding 2-hydroxy-4-alkenyloxy-acetophenone of Formula III. The compound of Formula III is then subjected to a Claisen rearrangement to yield a 2,4-dihydroxy-3-alkenyl-acetophenone compound of Formula IV. This rearrangement occurs on heating the compound of Formula III either neat or in a high boiling solvent, such as a halogenated hydrocarbon, e.g., dichlorobenzene, at from about 160° to about 210° C. The double bond in the compound of Formula IV may then be reduced, e.g., by catalytic hydrogenation with a catalyst such as Pd/C, to yield the corresponding saturated compound of Formula V.

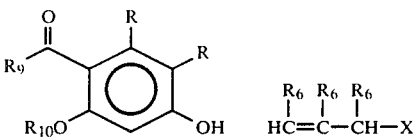

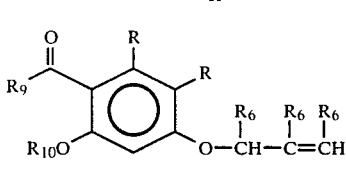

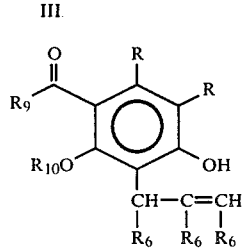

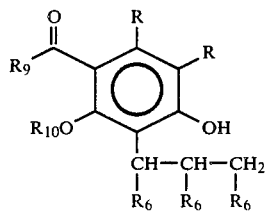

The compound of Formula V is then reacted with a dihaloalkane of Formula VIa or a dihaloalkene of Formula VIb wherein X, R and m have the meaning given previously, to yield a 4-(haloalkyloxy)-3-alkyl-2-hydroxyacetophenone compound of Formula VII. The reaction takes place by refluxing a mixture of the compounds of Formulae V and VIa or VIb in an inert solvent such as, for example, methylethylketone (MEK), acetone, tetrahydrofuran (THF), triglyme or dichloromethane in the presence of a base. The reflux temperature is preferably in the range of from about 60 to about 130° C. The base may be an alkali metal carbonate, for example, $Li_2CO_3$, $Na_2CO_3$ or $K_2CO_3$.

Specific examples of dihaloalkane compounds of Formula VIa are 1,3-dibromopropane, 2-methyl-1,3-dibromopropane, 2,2-dimethyl-1,3-dibromopropane, 3-chloro-2-chloromethyl-1-propene, 1,3-dibromobutane, 1,4-dibromobutane, 1,5-dibromopentane, 1,6-dibromohexane, 1,7-dibromoheptane, 1,8-dibromooctane, 1,9-dibromononane, 1,10-dibromodecane, and 1,12-dibromododecane. A specific example of a dihaloalkene compound of Formula VIb is 1,4-dibromo-2-butene.

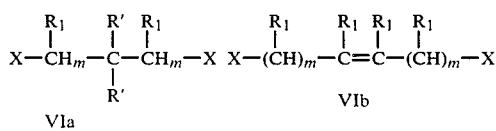

-continued

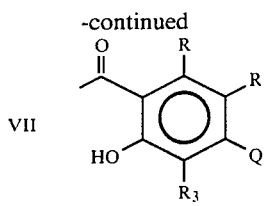

wherein Q is

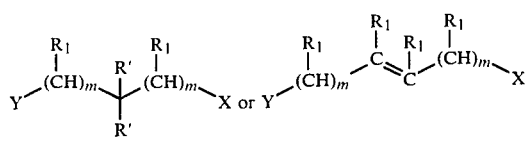

In lieu of the dihaloalkane or dihaloalkene, the compound of Formula IV or V may be reacted with an epihalohydrin, e.g., epichlorohydrin, under the same conditions to yield the 4-(2,3-epoxypropyloxy)-3-alkyl or 3-alkenyl-2-hydroxy-acetophenone compound of Formula VIII.

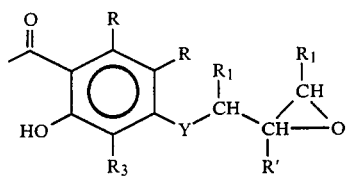

An alternative procedure is to react a compound of Formula II with a compound of Formula V to yield a 4-alkenyloxy-3-alkyl-2-hydroxy-acetophenone compound of Formula IX which is then epoxidized with an organic peracid such as, for example, m-chloroperbenzoic acid to give the compound of Formula VIII.

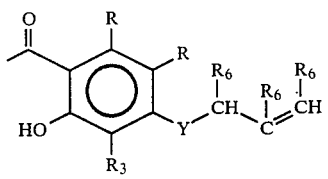

The reaction of a compound of Formula VII with a compound of Formula X, under the same conditions used to react a compound of Formula V with a compound of Formula VIa or VIb, gives compounds of Formulae XI or XII.

The reaction of a compound of Formula VIII with a compound of Formula X under the same conditions used to react a compound of Formula V with a compound of Formula VIa or VIb gives a compound of Formula XI wherein each m is 1.

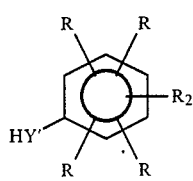

When Y' is —CH$_2$—, HY' is methyl. When Y' is

HY' is a protected aldehyde, such as, for example, a dithioacetal.

When Y' is methylene or carbonyl a stronger base such as, for example, lithium diisopropylamide or butyl lithium is employed in an inert solvent such as tetrahydrofuran with a suitable compound of Formula X.

A compound of Formula X is prepared by subjecting a compound of the Formula XIII:

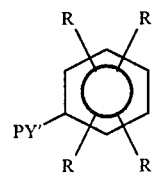

wherein P is H or a protecting group such as, for example, methyl, benzyl, p-nitrobenzyl or 3-(m-nitrophenyl)-1-phenyl-1-oxo-3-propyl to a Friedel-Crafts reaction with an acyl halide or an acid anhydride. Other compounds of Formulae XI and XII are obtained by reacting a compound of Formula VII with a compound of Formula X under the same conditions used to react a compound of Formula V with a compound of Formula VIa or VIb.

Alternatively, the compounds of Formulae XI and XII may be prepared by reacting a compound of Formula X with a compound of Formula VIa or VIb or an epihalohydrin under the same conditions as described for the preparation of the compound of Formula VII to give a compound of the Formula XIVa, XIVb or XIVc respectively. The latter are then reacted under the same conditions with a compound of Formula V to give compounds of Formulae XI or XII.

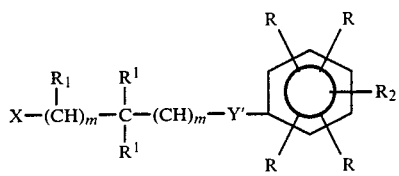

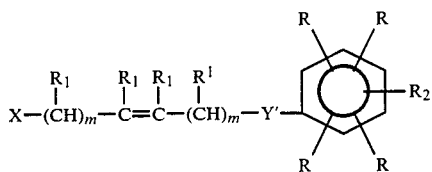

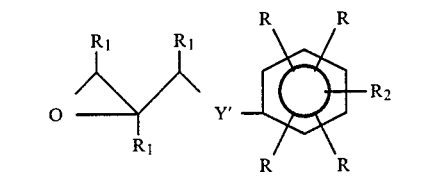

Alternatively, but less preferably, the compounds of Formulae IV or V, X and either VIa, VIb or epihalohydrin may be reacted simultaneously under the conditions described above for reacting a compound of Formula VIa or VIb or epihalohydrin with a compound of Formula X.

What is claimed is:

1. A Compound having the formula:

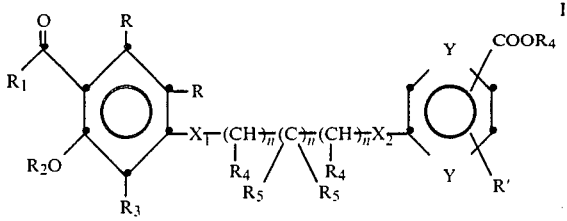

wherein:
each Y is independently selected from CR or N, but at least one Y but not both must be N;
each n is independently 0 to 6:
each R independently represents H, alkyl of 1 to 6 carbon atoms which is straight chain or branched, alkenyl of 2 to 6 carbon atoms which is straight chain or branched, trifluoromethyl, alkoxy of 1 to 6 carbon atoms which is straight chain or branched, SH, thioalkyl of 1 to 6 carbon atoms which is straight chain or branched, halogen, OH, amino, $N(R_4)_2$, $COOR_4$, $CH_2OR_4$, formyl, CN, trifluoromethylthio, or nitro (with the proviso that both R groups are not simultaneously OH, amino, $N(R_4)_2$, $COOR_4$, $CH_2OR_4$, formyl, CN, trifluoromethylthio, or nitro);
R' is H, alkyl of 1 to 6 carbon atoms which is straight chain or branched, alkenyl of 2 to 6 carbon atoms which is straight chain or branched, trifluoromethyl, alkoxy of 1 to 6 carbon atoms which is straight chain or branched, thioalkyl of 1 to 6 carbon atoms which is straight chain or branched, halogen, or trifluoromethylthio;
$R_1$ is H, alkyl of 1 to 6 carbon atoms which is straight chain or branched, or alkoxy of 1 to 6 carbon atoms which is straight chain or branched;
$R_2$ is H, alkyl of 1 to 6 carbon atoms which is straight chain or branched, $R_4CO$, or $R_4OCH_2$;
$R_3$ is alkyl of 1 to 6 carbon atoms which is straight chain or branched, alkenyl of 3 to 6 carbon atoms which is straight chain or branched, phenyl, or phenyl substituted by one or more R;
$R_4$ is independently H or alkyl of 1 to 6 carbon atoms which is straight chain or branched;
$R_5$ is independently H, OH, alkyl of 1 to 4 carbons, or both $R_5$'s are combined to create a doubly bonded oxygen (=O);
$X_1$ and $X_2$ are each independently oxygen, sulfur, sulfoxide, or sulfone;
and a pharmaceutically acceptable salt or acid addition salt thereof.

2. A Compound according to claim 1 wherein:
$X_1$ is O;
$X_2$ is O, S, SO, or $SO_2$;
one Y is N and the other is CH; and
each n is 1.

3. A Compound according to claim 1 said compounds having the formula:

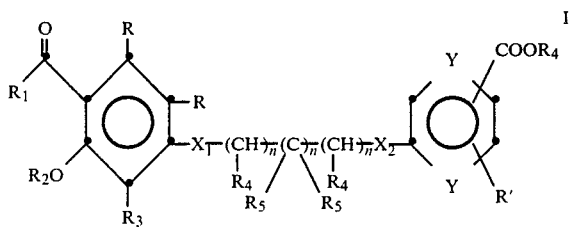

wherein each $R_1$ is alkyl of 1 to 6 carbon atoms which is straight chain or branched.

4. A compound of claim 1 wherein one Y is N and the other is CH, and $X_2$ is sulfur, sulfoxide, or sulfone.

5. A compound of claim 1 wherein $X_1$ is O and $X_2$ is S.

6. A compound of claim 1 wherein $X_1$ is O and $X_2$ is $SO_2$.

7. A compound of claim 1:
2-(3-(4-Acetyl-3-hydroxy-2-propylphenoxy)propylthio)-5-carboxypyridine;
Methyl 2-(3-(4-acetyl-3-hydroxy-2-propylphenoxypropylthio)pyridine-5-carboxylate;
Methyl 2-(3-(4-acetyl-3-hydroxy-2-propylphenoxypropylsulfonyl)pyridine-5-carboxylate; and
2-(3-(4-Acetyl-3-hydroxy-2-propylphenoxy)propylsulfonyl)-5-carboxypyridine.

8. A pharmaceutical composition, useful in antagonizing leukotriene action in mammals, comprising an amount of a compound of claim 1 effective as a leukotriene antagonist and a pharmaceutically acceptable carrier.

9. A method of antagonizing leukotriene action in a mammal which comprises administering to said mammal an effective amount of a compound of claim 1.

* * * * *